US006870613B1

(12) United States Patent
Tisone et al.

(10) Patent No.: US 6,870,613 B1
(45) Date of Patent: Mar. 22, 2005

(54) SIMULTANEOUS RECORDING OF MULTISPECTRAL FLUORESCENCE SIGNATURES

(76) Inventors: Gary C. Tisone, deceased, late of Albuquerque, NM (US); by Carolyn Tisone, legal representative, 9211 Eagle Rock, NE., Albuquerque, NM (US) 87122; Kevin R. Oldenburg, 6 Lafayette Pl., Chadds Ford, PA (US) 19317

( * ) Notice: Subject to any disclaimer, the term of this patent is extended or adjusted under 35 U.S.C. 154(b) by 275 days.

(21) Appl. No.: 10/094,256

(22) Filed: Mar. 7, 2002

Related U.S. Application Data

(60) Provisional application No. 60/273,999, filed on Mar. 7, 2001.

(51) Int. Cl.[7] .................................................. G01J 3/30
(52) U.S. Cl. ...................................................... 356/317
(58) Field of Search ................................. 356/316, 317, 356/417; 436/172; 422/82.08, 82.05; 250/458.1, 459.1, 461.1, 461.2

(56) References Cited

U.S. PATENT DOCUMENTS

| 5,612,540 | A | * | 3/1997 | Richards-Kortum et al. ...... 250/461.2 |
| 5,858,195 | A | * | 1/1999 | Ramsey ...................... 204/601 |
| 5,938,617 | A | | 8/1999 | Vo-Dinh |
| 6,066,459 | A | * | 5/2000 | Garini et al. .................. 435/6 |
| 6,087,182 | A | | 7/2000 | Jeng et al. |
| 6,485,703 | B1 | * | 11/2002 | Cote et al. .................... 424/9.1 |
| 6,571,118 | B1 | * | 5/2003 | Utzinger et al. ............ 600/476 |
| 6,652,809 | B1 | * | 11/2003 | Comley et al. .......... 422/82.05 |
| 2001/0033374 | A1 | * | 10/2001 | Hoyt .......................... 356/317 |

OTHER PUBLICATIONS

Collado, M.S., et al., "Determination of dexamethasone and two excipients (creatinine and propylparaben) in injections by using UV–spectroscopy and multivariate calibrations", *International Journal of Pharmaceutics*, 2001, pp. 205–211, vol. 229, Elsevier Science B.V.

De B. Harrington, P., et al., "Multivariate Curve Resolution of Wavelet and Fourier Compressed Spectra", *Analytical Chemistry*, Jul. 15, 2001, pp. 3247–3256, vol. 73, No. 14, American Chemical Society (also published on the Web May 26, 2001).

Ferraro, M.C.F., et al., "A spectrophotometric–partial least squares (PLS–1) method for the simultaneous determination of furosemide and amiloride hydrochloride in pharmaceutical formulations", *Journal of Pharmaceutical and Biomedical Analysis*, 2001, pp. 443–451, vol. 26, Elsevier Science B.V.

(List continued on next page.)

Primary Examiner—Zandra V. Smith
Assistant Examiner—Gordon J. Stock, Jr.
(74) Attorney, Agent, or Firm—Jeffrey D. Myers; Deborah A. Peacock; Vidal A. Oaxaca

(57) ABSTRACT

A method of and apparatus for generating a multivariate spectra over a predetermined excitation wavelength region comprising directing light spanning the region at a sample, simultaneously measuring intensities of resulting fluorescence spectra as a function of a plurality of fluorescence wavelengths produced at one or more excitation wavelengths in the region, and producing a multivariate spectra from the intensities, fluorescence wavelengths, and excitation wavelengths.

29 Claims, 6 Drawing Sheets

OTHER PUBLICATIONS

Goicoechea, H.C., et al., "Simultaneous determination of rifampicin, isoniazid and pyrazinamide in tablet preparations by multivariate spectrophotometric calibration", *Journal of Pharmaceutical and Biomedical Analysis,* 1999, pp. 681–686, vol. 20, Elsevier Science B.V.

Goicoechea, H.C., et al., "Simultaneous multivariate spectrophotometric analysis of paracetamol and minor components (diphenhydramine or phenylpropranolamine) in tablet preparations", *Journal of Pharmaceutical and Biomedical Analysis,* 1999, pp. 255–261, vol. 20, Elsevier Science B.V.

Goicoechea, H.C., et al., "Sustained prediction ability of net analyte preprocessing methods using reduced calibration sets. Theoretical and experimental study involving the spectrophotometric analysis of multicomponent mixtures", *Analyst,* 2001, pp. 1105–1112, vol. 126, The Royal Society of Chemistry.

Hansen, P.W., et al., "Detection of Specific Sugars in Dairy Process Samples Using Multivariate Curve Resolution", *Journal of Dairy Science,* 1999, pp. 1351–1360, vol 82, No. 7.

Luis, M.L., et al., "Simultaneous Determination of Chlorthalidone and Spironolactone with Univariate and Multivariate Calibration: Wavelength Range Selection", *Journal of AOAC International,* 1999, pp. 1054–1063, vol. 82, No. 5.

Martos, N.R., et al., "Simultaneous spectrofluorimetric determination of (acetyl) salicylic acid, codeine and pyridoxine in phamaceutical preparations using partial least–squares multivariate calibration", *Journal of Pharmaceutical and Biomedical Analysis,* 2000, pp. 837–844, vol. 23, Elsevier B.V.

Mendieta, J., et al., "Multivariate Curve Resolution: A Possible Tool in the Detection of Intermedicate Structures in Protein Folding", *Biophysical Journal,* Jun., 1998, pp. 2876–2888, vol., 74, Biophysical Society.

Rhiel, M., et al., "Nondestructive Near–Infrared Spectroscopic Measurement of Multiple Analytes in Undiluted Samples of Serum–Based Cell Culture Media", *Biotechnology and Bioengineering,* Jan. 5, 2002, pp. 73–82, vol. 77, No. 1, John Wiley & Sons, Inc.

Ribone, M.E., et al., "Determination of the minor component bromhexine in cotrimoxazole–containing tablets by absorption spectrophotometry and partial least–squares (PLS–1) multivariate calibration", *Journal of Pharmaceutical and Biomedical Analysis,* 2000, pp. 591–595, vol. 23, Elsevier Science B.V.

Rubenstein, R., et al., "Detection and Discrimination of $PrP^{SC}$ by Multi–spectral Ultraviolet Fluorescene", *Biochemical and Biophysical Research Communications,* 1998, pp. 100–106, vol. 246, Academic Press.

Vives, M., et al., "Three–Way Multivariate Curve Resolution Applied to Speciation of Acid–Base and Thermal Unfolding Transitions of an Alternating Polynucleotide", *Bioploymers,* 2001, pp. 477–488, vol. 59, John Wiley & Sons, Inc.

* cited by examiner

SIMULTANEOUS RECORDING OF MULTISPECTRAL FLUORESCENCE SIGNATURES

CROSS-REFERENCE TO RELATED APPLICATIONS

This application claims the benefit of the filing of U.S. Provisional Patent Application Ser. No. 60/273,999, entitled "Technique for Simultaneous Recording of Multispectral Fluorescence Signatures for Excitation and Fluorescence Wavelengths", filed on Mar. 7, 2001, and the specification thereof is incorporated herein by reference.

BACKGROUND OF THE INVENTION

1. Field of the Invention (Technical Field)

The present invention relates to multispectral fluorescence signatures for identification of chemical and biological materials.

2. Background Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

The use of multispectral signatures along with multivariate analysis has become a viable technique for the identification of chemical and biological materials in mixtures and with strong background signals. In this technique a three-dimensional spectral signature is generated over a predetermined excitation wavelength by measuring the intensity of the resulting fluorescent spectra as a function of fluorescent wavelength that is produced at a number of excitation wavelength. An example of a spectral signature is shown in FIG. 1. The excitation source can be a tunable laser or a continuous light source such as a high-pressure xenon lamp filtered by a monochromator or suitable narrow band filters. The usual method of measurement requires that the excitation wavelength be stepped through a set of wavelengths.

The following references are noted and incorporated herein by reference: H. C. Goicoechea, et al., *J. Pharm. Biomed. Anal.* 20(1–2):255–61 (1999); H. C. Goicoechea, et al., *J. Pharm. Biomed. Anal.* 20(4):681–6 (1999); M. L. Luis, et al., *J. AOAC Int.* 82(5):1054–63 (1999); P. W. Hansen, et al., *J. Dairy Sci.* 82(7):1351–60 (1999); J. Mendieta, et al., *Biophys. J.* 74(6):2876–88 (1998); M. E. Ribone, et al., *J. Pharm. Biomed. Anal.* 23(2–3):591–5 (August 2000); N. R. Martos, et al., *J. Pharm. Biomed. Anal.* 23(5):837–44 (October 2000); H. C. Goicoechea, et al., *Analyst* 126(7):1105–12 (July 2001); P. B. Harrington, et al., *Anal. Chem.* 73(14):3247–56 (July 2001); M. Rhiel, et al., *Biotechnol. Bioeng.* 5;77(1):73–82 (January 2002); M. Vives, et al., *Biopolymers* 59(7):477–88 (December 2001); M. S. Collado, et al., *Int. J. Pharm.* 23;229(1–2):205–11 (October 2001); M. C. Ferraro, et al., *J. Pharm. Biomed. Anal.* 26(3):443–51 (October 2001); R. Rubenstein, et al., *Biochem. Biophys. Res. Commun.* 8;246(1):100–6 (1998); J. S. Wagner, et al., *Computers in Physics* 10(2):114 (1996); U.S. Pat. No. 6,087,182, to Jeng, et al.; and U.S. Pat. No. 5,938,617, to Vo-Dinh.

The present invention provides a method for measuring the spectral signature by simultaneous recording of the fluorescence spectra at all excitation wavelengths.

SUMMARY OF THE INVENTION
(DISCLOSURE OF THE INVENTION)

The present invention is of a method of and apparatus for generating a multivariate spectra over a predetermined excitation wavelength region, comprising: directing light spanning the region at a sample; simultaneously measuring intensities of resulting fluorescence spectra as a function of a plurality of fluorescence wavelengths produced at one or more excitation wavelengths in the region; and producing a multivariate spectra from the intensities, fluorescence wavelengths, and excitation wavelengths. In the preferred embodiment, the multivariate spectra are employed to identify one or more components of the sample, preferably to identify and measure a plurality of components of the sample by assuming that the multivariate spectra is a linear combination of expected multivariate spectra of the plurality of components. The steps may be repeatedly performed to determine reaction rates between the plurality of components in a chemical or biological reaction, or in medical diagnostic procedures or drug development procedures. Directing preferably employs an excitation source such as a tunable laser or a continuous light source, most preferably a high-pressure xenon lamp filtered by a monochromator or narrow band filter. Measuring comprises simultaneously measuring intensities of resulting fluorescence spectra as a function of a plurality of fluorescence wavelengths produced at a plurality of excitation wavelengths in the region. The sample may be in a cuvette or microwell plate (preferably with a clear bottom of fused silica, quartz, or other material transparent in the desired spectral range). The microwell plate preferably contains from 1 to 9600 wells, most preferably 12, 24, 48, 96, 384, or 1536. Processing is preferably accomplished for each well of the plate in less than approximately 1 minute, more preferably less than approximately 5 seconds, and most preferably less than approximately 1 second. Most preferably processing is accomplished for each well of the plate simultaneously. Measuring employs a detector such as a photomultiplier tube, CCD camera, CCD chip, fiber optic array impinging upon a photomultiplier or CCD device, or microscope. The sample preferably has a volume between approximately 1 picoliter to 10 milliliters.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings:

FIG. 6($b$) is a contour plot of the FBS signature.

DESCRIPTION OF THE PREFERRED EMBODIMENTS (BEST MODES FOR CARRYING OUT THE INVENTION)

Figure 1:
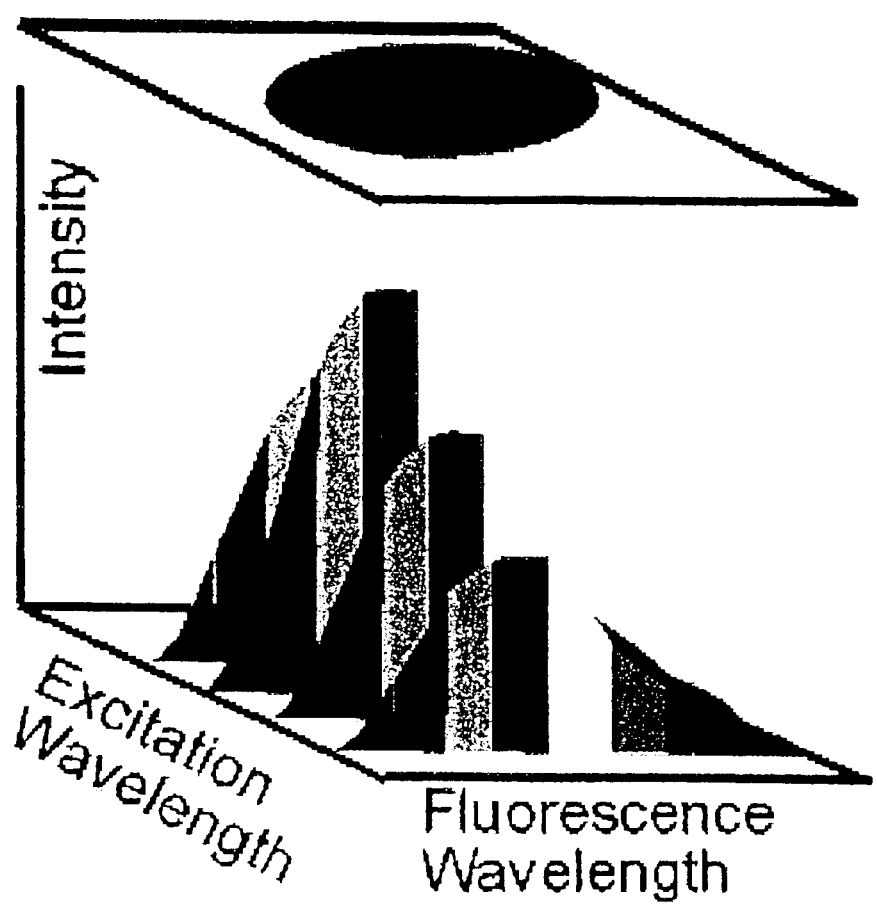
FIG. 1 is a multispectral fluorescent signature showing fluorescent intensity as a function of excitation and fluorescent wavelength.

To reiterate, the use of multispectral signature along with multivariate analysis has become a viable technique for the identification of chemical and biological materials in mixtures and with strong background signals. In this technique a three-dimensional spectral signature is generated over a predetermined excitation wavelength by measuring the intensity of the resulting fluorescent spectra as a function of fluorescent wavelength that is produced at a number of excitation wavelength. An example of a spectral signature is shown in FIG. 1. The excitation source can be a tunable laser or a continuous light source such as a high-pressure xenon lamp filtered by a monochromator or suitable narrow band filters. The usual method of measurement requires that the excitation wavelength be stepped through a set of wavelengths.

The present invention is of a method and apparatus for measuring the special signature by simultaneous recording of the fluorescence spectra at all excitation wavelengths.

Figure 2:
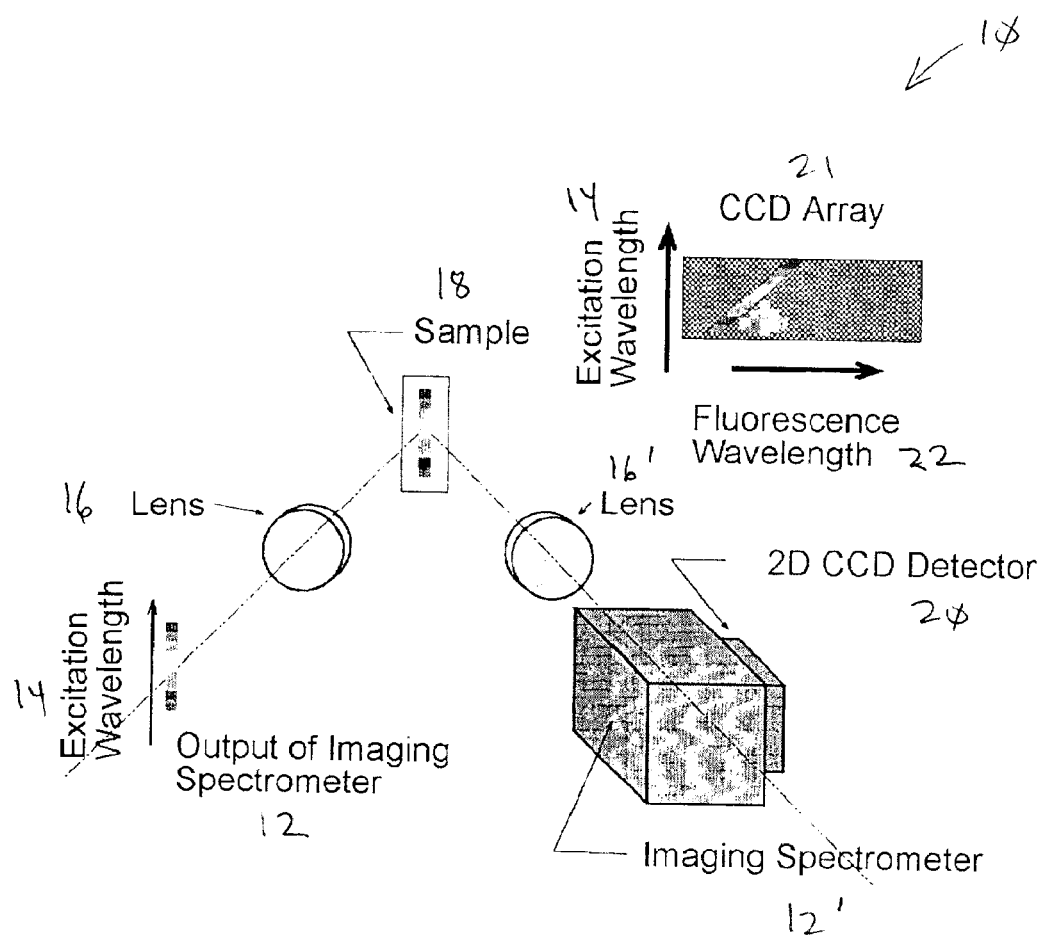
FIG. 2 is a block diagram for two-dimensional imaging of excitation and fluorescent wavelengths to obtain a total fluorescent signature.

The preferred method and apparatus 10 of the present invention for performing the measurement using monochromators (spectrometers) is shown in FIG. 2. The light from a continuous light source is focused onto the entrance slit of a monochromator that is set at a wavelength near the center of the desired excitation wavelength region 14. In the usual configuration with the output slit parallel to the entrance slit, a narrow band of light at the wavelength setting passes through the slit. If the slit is removed, a broad continuous spectra is emitted from the monochromator 12. A slit perpendicular to the input slit is used to define the width of the light and the resulting continuous excitation is shown in FIG. 2. The resulting excitation spectra are imaged by a lens system 16 on the sample 18 wherein each vertical position, $z_s$, represents a corresponding excitation wavelength, $\lambda_e$. At each excitation wavelength, $\lambda_e$, fluorescence as a function of wavelength, $\lambda_f$, is generated. The fluorescence, along with the scattered excitation light, is imaged by a lens system 16' onto the entrance slit of an imagining spectrometer 12'. The distance along the entrance slit is correlated with an excitation wavelength. The imaging spectrometer disperses the fluorescence in a direction perpendicular to the entrance slit and the excitation wavelength that is imaged on a two-dimensional detector 20. The resulting spectral signature 21 is shown in the inset in FIG. 2. The signature is recorded over a range of excitation wavelengths 14 and fluorescence wavelengths 22 without scanning the excitation monochromator or the imaging spectrometer thus producing a signature in a time much less than that required when the excitation is scanned.

The excitation wavelength(s) are preferably between approximately 190 nm to 900 nm, and the emission wavelength(s) are also preferably between approximately 190 nm to 900 nm. Preferably, both excitation wavelength and emission wavelength can be tuned in increments from approximately 0.1 nm to 20 nm.

The invention is useful, for example, to determine the amount and/or concentration of a small fluorescent molecule (molecular weight between 100 daltons and 10,000 daltons) in a complex solution such as, e.g., human serum. The invention can also be used to determine the degree of protein crystallization based on the inherent changes in fluorescence that the protein undergoes during crystallization. It can be used to determine the amount of a small molecule directly bound to serum proteins or free in solution. It can further be used to determine the binding interaction between a small molecule and a protein, solid surface, or nucleic acid.

Figure 5:
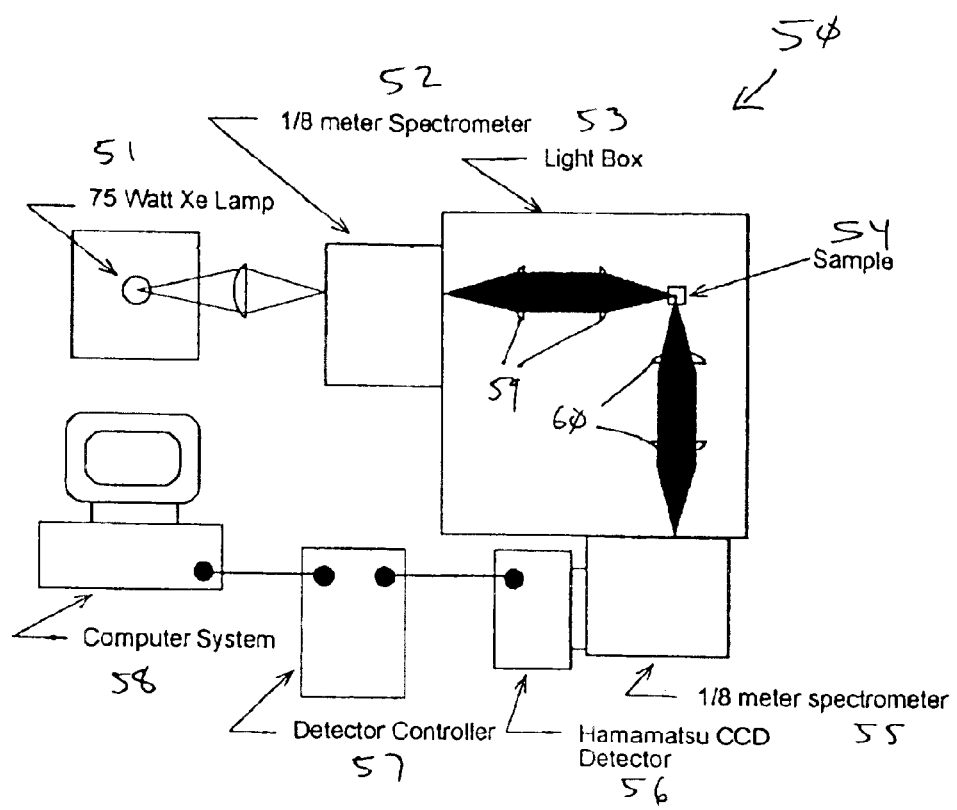
FIG. 5 is a block diagram of a system according to the invention to measure fluorescent signatures simultaneously as a function of excitation and fluorescence wavelengths.

A schematic diagram of an exemplary instrument 50 according to the invention is shown in FIG. 5. The excitation light source for the system is a high pressure, 75 watt, Xe arc lamp 51 that gives light that is continuous in wavelength over the wavelength of interest (250 nm to 600 nm). The lamp is an Oriel Model 6257 in an Oriel series Q lamp housing, Model 60064 with a F/1 fused silica condensing lens. The continuous light from this source is focused onto the entrance slit of a ⅛ meter imaging spectrometer 52 (CVI Model CMSP110). The spectrometer is rotated 90 degrees to give a dispersed spectrum in the vertical direction as shown in FIG. 2. The center wavelength of the dispersed spectrum can be set with the spectrometer. The dispersed output of spectrometer is then focussed into a sample cuvette 54 within a light box 53 by a fused silica lens system 59 as shown in FIG. 5. Fused silica allows measurements in the near UV part of the spectrum (220 nm). In this system the sample is in liquid suspension in a 1 cm×1 cm fused silica or UV transmitting plastic cells, however, the system is not limited to measurements in a cell. Measurements can be made of samples on a solid substrate or with samples in a microliter plate. The fluorescence from the sample near the waste or best focus of the excitation spectrum at 90 degrees is focussed onto the entrance slit of the detection spectrometer 55 using a set of silica lenses 60. In this instrument, the lens systems for excitation and detection are identical but this is not necessary for the operation of the system. The detection spectrometer is identical to the excitation spectrometer except that the exit slit is at 90 degrees to the entrance slit. The dispersion of this spectrometer is at 90 degrees to the direction of dispersion of the excitation spectrometer. The fluorescence from the sample at each excitation wavelength is dispersed and imaged at the exit plane of the detection spectrometer. This produces the two dimensional spectral signature as previously described. This image is recorded on a two-dimensional CCD array 56. In this instrument the detector was a Hamamatsu cooled, back thinned CCD with 512 by 256 pixels (Model S7032-0908). After recording the light for a given integration time, the resulting signal is read out using a detector controller 57 and a computer system 58.

Figure 6:
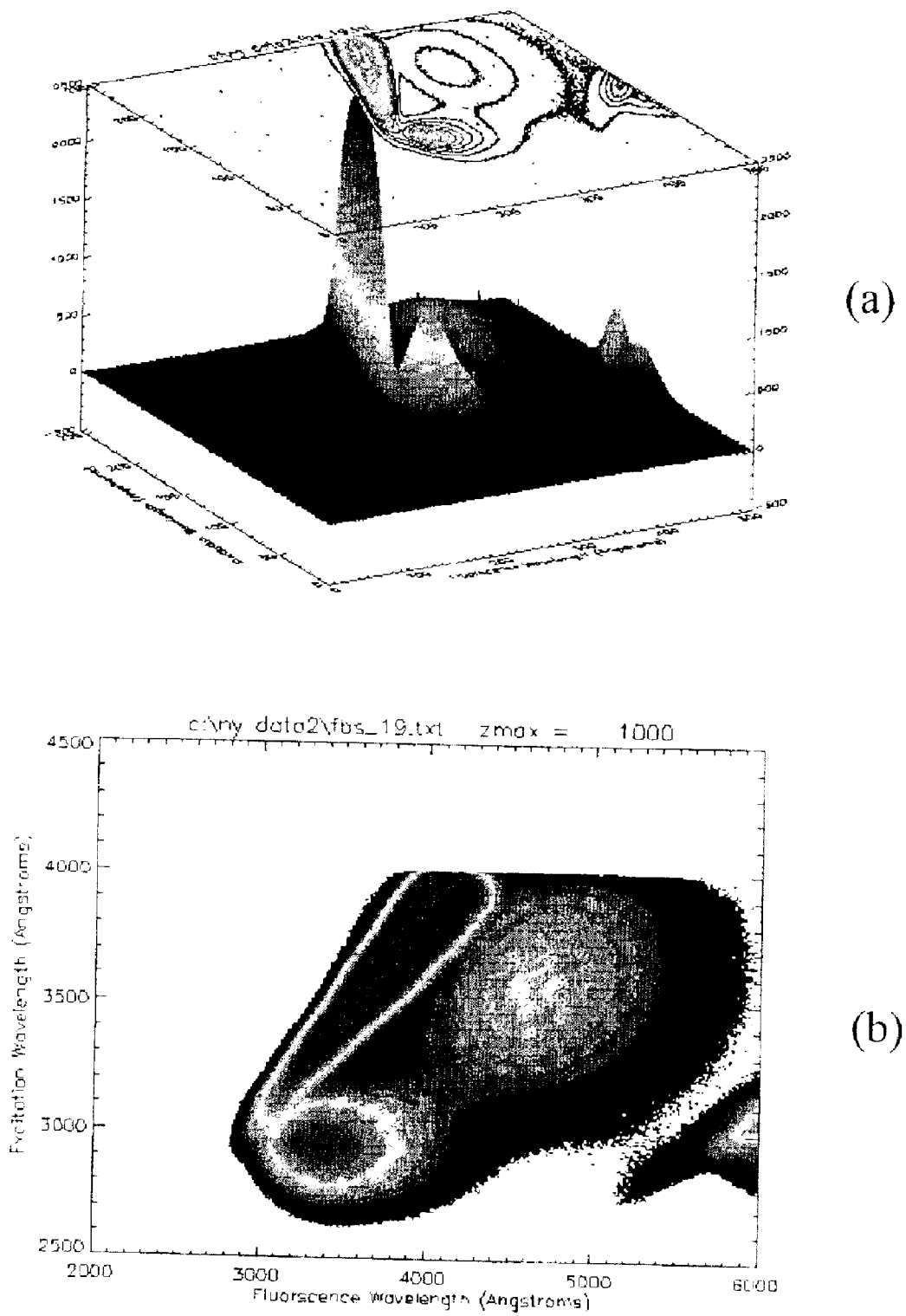
FIG. 6($a$) is a spectral signature of fetal bovine serum (FBS) recorded using the system of FIG. 5 showing a three-dimensional representation of the signature and a contour plot obtained by projection on the top surface; the fluorescence wavelength is measured along the x-axis and the excitation wavelength is measured along the y-axis; the fluorescent intensity at an excitation and fluorescent wavelength is measured in the z-axis.

An example of a spectral signature taken by this instrument is shown in FIGS. 6($a$) and ($b$). The spectra was taken from a solution of 20 $\mu$l FBS (fetal bovine serum) in 1 ml of PBS (phosphate buffered solution). 3 ml of the solution was placed in a standard 1 cm×1 cm×3 cm fused silica cell. The cell was placed at the focus of the excitation light and the focus of the detection optics as shown in the figures. The excitation spectrometer used a 300 line/mm grating that was set to a center wavelength of 300 nm and the detection spectrometer used a 600 line/mm grating that was set for a center wavelength of 350 nm. An integration time of 50 sec was used to obtain the signature. FIG. 6(a) shows the three-dimensional signature recorded on the CCD array as a function of pixel location. The excitation axis has 256 pixels while the fluorescent axis has 512 pixels. The z-axis is a measure of the fluorescent intensity. The top plane has the projection of the three-dimensional image to produce a color contour plot of the signature. In FIG. 6(b) a contour plot of the signature as a function of excitation wavelength and fluorescence wavelength is shown.

The signatures of several biological materials or chemical compounds can be taken and used as a basis set to determine the composition of an unknown solution. This includes an unknown with one or more components of the basis set.

Figure 3:
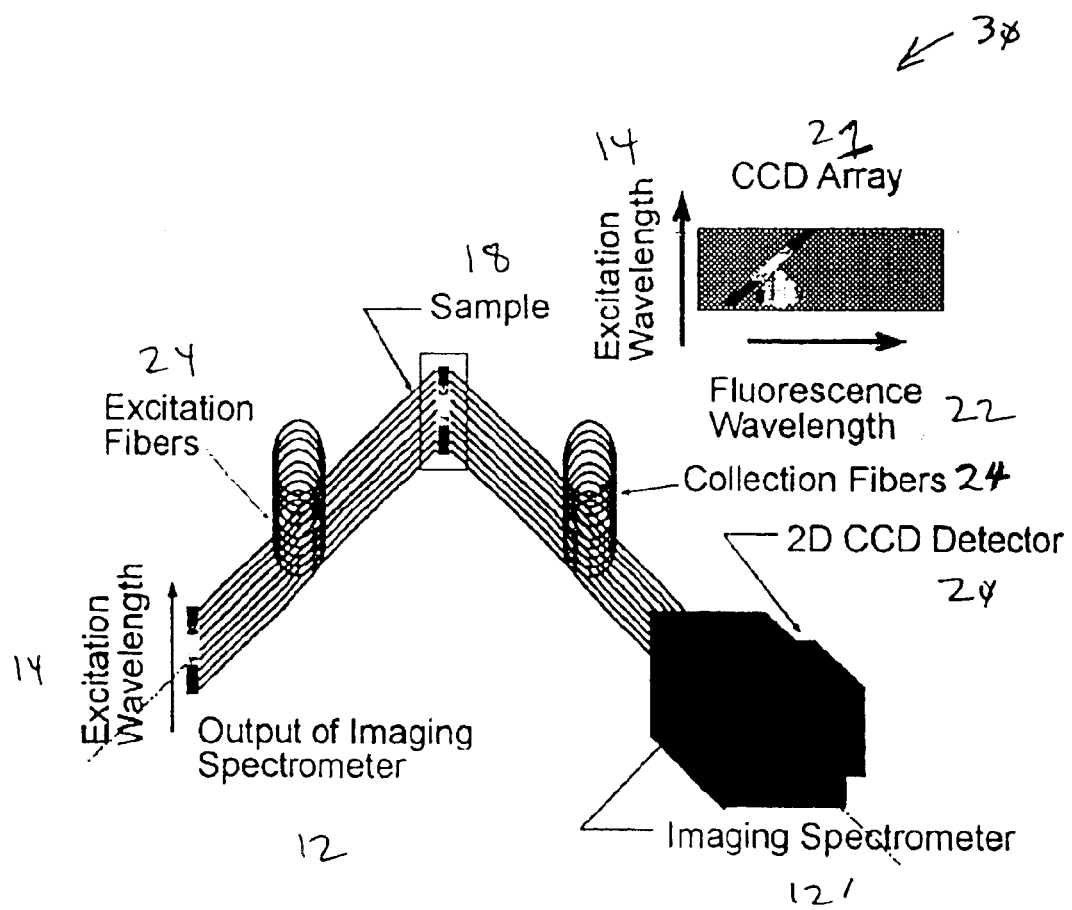
FIG. 3 is a block diagram for two-dimensional imaging of a fluorescent signature using fiber bundles for the excitation and collection.

The above-described preferred implementation of the invention is by direct imaging of the output of the excitation monochromator and then reimaging the fluorescence onto the detection spectrometer. Direct imaging is not always possible or convenient. A variation 30 of the above process and apparatus uses fiber optic bundles 24,24' as shown in FIG. 3. The excitation light is collected by a linear array of fibers 24 either directly or imaging with a lens system. The fibers collect light at different wavelengths. The excitation is then transmitted through the fiber to the sample. The emerging light is directed onto the sample with or without a lens system. The wavelength relationship of the transmitting fibers is preserved. The resulting fluorescence is collected by a fiber array 24'. Each collection fiber has a unique relationship with the excitation light. The light from the collection fiber is then collected by an imaging spectrometer where the fluorescence is dispersed perpendicular to the slit. The fibers are aligned along the slit and are correlated with the excitation light. In this manner a signature that is two dimensional in excitation and fluorescence is measured.

Figure 4:
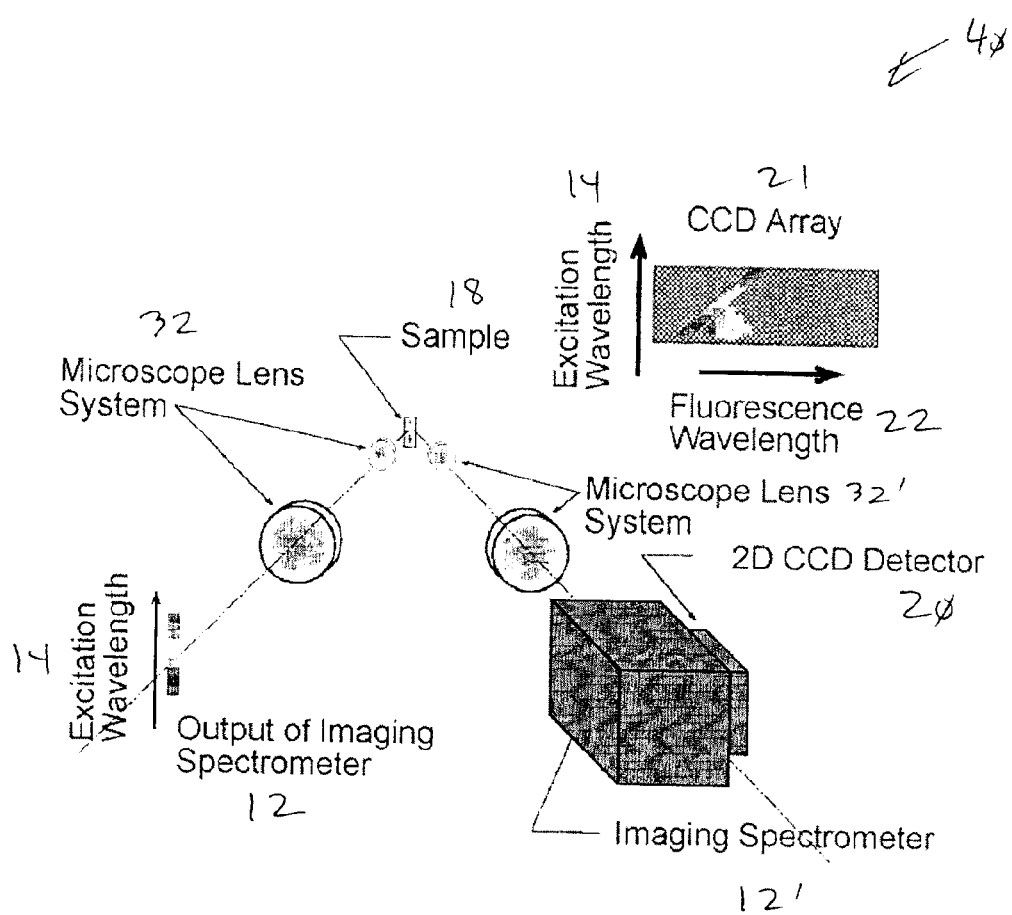
FIG. 4 is a block diagram of two-dimensional imaging of a fluorescent signature using a microscope lens system for the excitation and collection.

If one is to make measurements on very small samples, micro or nanoliters of material, then a continuous excitation spectra on the scale of the samples is preferably generated. As shown in the system 40 of FIG. 4, it is then preferred that the image of the excitation light be reduced to the size of the sample by imaging through a microscope lens system 32,32'. The image of the fluorescence is magnified by the microscope lens system. In this figure two separate microscope systems are shown; however, in an alternative embodiment, the excitation and fluorescence can be made co-linear with the use of a beam splitter to introduce the excitation light into the microscope system. The fluorescence from the sample as a function of excitation wavelength is imaged onto the slit of the detection spectrograph and is then dispersed onto the two-dimensional CCD array and recorded.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A method of generating multivariate spectra over a predetermined region of multiple excitation wavelengths, the method comprising the steps of:

directing light having the multiple excitation wavelengths at a sample simultaneously for each wavelength;

dispersing the multiple excitation wavelengths spatially along the sample;

detecting simultaneously fluorescence wavelengths generated by the sample at each of a plurality of the predetermined excitation wavelengths; and producing multivariate spectra of intensities of the fluorescence wavelengths and the excitation wavelengths.

2. The method of claim 1 wherein the producing step comprises simultaneously measuring intensities of the resulting fluorescence spectra as a function of a plurality of fluorescence wavelengths produced at a plurality of the excitation wavelengths in the region.

3. The method of claim 1 wherein the directing step comprises directing light at a sample in a cuvette.

4. The method of claim 1 wherein the detecting step comprises employing a detector selected from the group consisting of photomultiplier tubes, CCD cameras, CCD chips, fiber optic arrays impinging upon a photomultiplier or CCD device, and microscopes.

5. The method of claim 1 wherein the directing step comprises directing light at a sample having a volume between approximately 1 picoliter to 10 milliliters.

6. The method of claim 1 additionally comprising the step of employing the multivariate spectra to identify one or more components of the sample.

7. The method of claim 6 wherein the employing step comprises employing the multivariate spectra to identify and measure a plurality of components of the sample by assuming that the multivariate spectra is a linear combination of expected multivariate spectra of the plurality of components.

8. The method of claim 7 wherein the method is repeatedly performed to determine reaction rates between the plurality of components in a chemical or biological reaction.

9. The method of claim 7 wherein the method is used in a procedure selected from the group consisting of medical diagnostic procedures and drug development procedures.

10. The method of claim 1 wherein the directing step comprises employing an excitation source selected from the group consisting of tunable lasers and continuous light sources.

11. The method of claim 10 wherein the directing step comprises employing a high-pressure xenon lamp filtered by a means selected from the group consisting of monochromators and narrow band filters.

12. The method of claim 1 wherein the directing step comprises directing light at a sample in a microwell plate.

13. The method of claim 12 wherein in the directing step the microwell plate has a clear bottom.

14. The method of claim 13 wherein in the directing step the microwell plate has a clear bottom of a material selected from the group consisting of fused silica, quartz, and materials transparent in a desired spectral range.

15. The method of claim 13 wherein in the directing step the microwell plate contains from 1 to 9600 wells.

16. The method of claim 13 wherein in the directing step the microwell plate contains a number of wells selected from the group consisting of 12, 24, 48, 96, 384, and 1536.

17. The method of claim 13 wherein the method is accomplished for each well of the plate in less than approximately 1 minute.

18. The method of claim 17 wherein the method is accomplished for each well of the plate in less than approximately 5 seconds.

19. The method of claim 18 wherein the method is accomplished for each well of the plate in less than approximately 1 second.

20. The method of claim 18 wherein the method is accomplished for each well of the plate simultaneously.

21. An apparatus for generating multivariate spectra over a predetermined region of multiple excitation wavelengths, said apparatus comprising:
- a light directing, and multiple excitation wavelength dispersing, system for spatially dispersing the wavelengths in said region along a sample;
- a multiple fluorescence wavelength detector for detecting simultaneously fluorescence wavelengths generated by said sample at each of a plurality of said predetermined excitation wavelengths; and
- a system for producing multivariate spectra of intensities of said fluorescence wavelengths and said excitation wavelengths.

22. The apparatus of claim 21 wherein said detector comprises a detector selected from the group consisting of photomultiplier tubes, CCD cameras, CCD chips, fiber optic arrays impinging upon a photomultiplier or CCD device, and microscopes.

23. The apparatus of claim 21 wherein said light directing system comprises an excitation source selected from the group consisting of tunable lasers and continuous light sources.

24. The apparatus of claim 23 wherein said light directing system comprises a high-pressure xenon lamp filtered by a means selected from the group consisting of monochromators and narrow band filters.

25. The apparatus of claim 21 additionally comprising a microwell plate containing the sample.

26. The apparatus of claim 25 wherein said microwell plate has a clear bottom.

27. The apparatus of claim 26 wherein said microwell plate has a clear bottom of a material selected from the group consisting of fused silica, quartz, and materials transparent in a desired spectral range.

28. The apparatus of claim 26 wherein said microwell plate contains from 1 to 9600 wells.

29. The apparatus of claim 26 wherein said microwell plate contains a number of wells selected from the group consisting of 12, 24, 48, 96, 384, and 1536.

* * * * *